United States Patent
Jassem et al.

(10) Patent No.: US 11,471,550 B2
(45) Date of Patent: Oct. 18, 2022

(54) VOLATILE LIQUID DISPENSING SYSTEM

(71) Applicant: Fragrance Delivery Technologies Private Limited, Maharashtra (IN)

(72) Inventors: K M Hydros Jassem, Dubai (AE); Puthiya Kottal Saquib Mohamed, Kannur (IN)

(73) Assignee: Fragrance Delivery Technologies Private Limited, Maharashtra (IN)

( * ) Notice: Subject to any disclaimer, the term of this patent is extended or adjusted under 35 U.S.C. 154(b) by 0 days.

(21) Appl. No.: 16/312,266

(22) PCT Filed: May 22, 2017

(86) PCT No.: PCT/IN2017/050194
§ 371 (c)(1),
(2) Date: Dec. 20, 2018

(87) PCT Pub. No.: WO2017/221264
PCT Pub. Date: Dec. 28, 2017

(65) Prior Publication Data
US 2019/0231917 A1    Aug. 1, 2019

(30) Foreign Application Priority Data

Jun. 20, 2016 (IN) .............................. 201621021000

(51) Int. Cl.
*A61L 9/12*    (2006.01)
*A01M 1/20*    (2006.01)
*A61L 9/04*    (2006.01)

(52) U.S. Cl.
CPC .............. *A61L 9/12* (2013.01); *A01M 1/2044* (2013.01); *A61L 9/042* (2013.01); *A61L 2209/133* (2013.01); *A61L 2209/15* (2013.01)

(58) Field of Classification Search
CPC . A61L 9/12; A61L 9/127; A61L 9/042; A61L 2209/133; A61L 2209/15; A01M 1/2044; B67D 7/00
(Continued)

(56) References Cited

U.S. PATENT DOCUMENTS 4,878,615 A * 11/1989 Losi .......................... A61L 9/12
239/45
5,533,705 A    7/1996 Zlotnik et al.
(Continued)

OTHER PUBLICATIONS

International Search Report received in connection with International Patent Application No. PCT/IN2017/050194, dated Aug. 24, 2017.

*Primary Examiner* — Cody J Lieuwen
(74) *Attorney, Agent, or Firm* — Knobbe, Martens, Olson & Bear, LLP (57) ABSTRACT

Disclosed is a volatile liquid dispensing system that includes a dispenser and a refill unit. The dispenser is mounted on a predefined surface. The dispenser includes a front cover and a rear cover. The refill unit is removably secured inside the dispenser thereby maintaining a predefined gap therebetween. The refill unit includes a refill cover. The refill cover includes a fragrance reservoir and a collection device enclosed therein. The fragrance reservoir is formed by a gas shell and a fragrance shell. The fragrance reservoir is positioned in a predefined orientation with respect to the mounting surface. The collection device is positioned adjacent to the fragrance reservoir such that a predefined gap is maintained therebetween. The collection device is enclosed in the refill cover such that a predefined gap is maintained therebetween thereby allowing evaporation of the volatile liquid from all sides of the collection device.

10 Claims, 6 Drawing Sheets

(58) Field of Classification Search
USPC .................................................. 239/43, 51.5
See application file for complete search history.

(56) References Cited

U.S. PATENT DOCUMENTS

| | | | |
|---|---|---|---|
| 5,785,688 | A | 7/1998 | Joshi et al. |
| 7,681,809 | B2 | 3/2010 | Maget et al. |
| 7,922,104 | B2 | 4/2011 | Zlotnik et al. |
| 8,178,048 | B2 | 5/2012 | Zlotnik et al. |
| 8,733,597 | B2 | 5/2014 | Fitzpatrick et al. |
| 2005/0023371 | A1* | 2/2005 | Joshi ................ A61L 9/127 239/60 |
| 2005/0263609 | A1* | 12/2005 | Joshi ................ A61L 9/127 239/6 |
| 2007/0210101 | A1* | 9/2007 | Hammond .......... A01M 1/2044 222/3 |
| 2008/0290186 | A1* | 11/2008 | Zlotnik ............... A61L 9/127 239/43 |
| 2012/0187217 | A1* | 7/2012 | Maget ................ A61L 9/12 239/326 |
| 2015/0076716 | A1* | 3/2015 | Roemburg .......... B05B 17/0653 261/78.2 |
| 2016/0144064 | A1* | 5/2016 | Santini ............... A61L 9/127 239/6 |

* cited by examiner

VOLATILE LIQUID DISPENSING SYSTEM

FIELD OF THE INVENTION

The present invention relates generally to fluid dispensing systems and more particularly, to a volatile liquid dispensing system.

BACKGROUND OF THE INVENTION

The fragrance delivery systems are used to emit fragrance/air scent to treat an environment in public as well as institutional areas. In one of the class of the fragrance delivery system, a liquid fragrance/volatile liquid is delivered on to an emanating surface and evaporates into the environment therefrom. In order for these systems to perform efficiently, the volatile liquid needs to be expelled out of a storage device and delivered on to the emanation device/surface for evaporation into the environment.

The fragrance delivery systems that uses forced manner for expelling volatile liquid utilizes gas, gravity or capillary action to move a flexible membrane or by direct action/pressurization of the fragrance/liquid thereby facilitating expelling of the fragrance from a storage reservoir on to the emanating surface. For example, U.S. Pat. No. 7,922,104 (B2) discloses a gravity driven fluid supply vessel for maintaining a supply of volatile liquid in a storage cup containing an edge portion of a wick for broadcasting the volatile liquid along the evaporation chamber.

Reference may be made to U.S. Pat. No. 7,681,809 (B2) that discloses a device for achieving a controlled low emanation rate of small volumes of liquid solutions. The device has an electro-chemical gas generator that exerts pressure on a bladder containing liquid solution which in turn forces the liquid solution from the bladder onto the pad for release to the environment. Another U.S. Pat. No. 5,785,688 (A) discloses a fluid delivery apparatus that includes a housing, a fluid reservoir disposed within the housing for storing the fluid, a pump or pressurized chamber for pressurizing a driving gas and exerting a force on the fluid reservoir to expel the fluid reservoir's contents, and a needle or absorbent pad fluidically communicating with the reservoir. However, in such systems even though the pumping of the volatile liquid/fragrance liquid from the reservoir to the emanating surface happens at controlled rates, the liquid contents pumped out does not evaporate efficiently into a room either due to insufficient pad area or insufficient air flow caused by a geometrical configuration of a product thereby reducing net fragrance in the room.

Since only fraction of what is being pumped out is evaporating, there is tendency of the fragrance to collect on the emanating surface and at some point, can leak out of the system due to over saturation of the emanating device/surface. There are systems that overcome this drawback by using continuous/intermittent forced evaporation with heat/fan. For example, U.S. Pat. No. 5,533,705 (A) discloses a drive for providing an air stream for generating vapor from a wick or ceramic wafers or discs containing vaporizable deodorant. Another U.S. Pat. No. 8,178,048 (B2) discloses a dispenser fixture for dispersing aromatic vapors into a facility that includes a motor driven fan and fixtures for supplying and controlling electrical current for powering the fan motor. However, these systems are not economical and do not present a market opportunity as the battery life is very low or require AC power that is not available at all locations. There are also issues of decrease in pumping rates in systems that have flexible bag shaped reservoirs due to bag resistance or inability of the membrane to reach the liquid reservoir side snugly thus not expelling all the liquid from the reservoir at low internal pressures.

In existing designs of the fragrance delivery systems, the emanating surfaces are either wound around other sub components or held very close to the other subcomponents. For example, U.S. Pat. No. 8,733,597 (B2) discloses a liquid dispenser that comprises a ratchet assembly, a rotor assembly, a reservoir assembly, and a drive mechanism. Another U.S. Pat. Pub. No. US2016144064 (A1) discloses a fragrance delivery device that comprises a housing including at least one sidewall, a base member coupled with the housing, and an absorbent member receivable in the housing and disposed above the base member. However, if the emanating surfaces are wound around other subcomponents, due to circular nature of the emanating surface air flow to the inner surface is restricted. In case the emanating surface is held very close to the other subcomponents, the air flow is restricted to only one side due to insufficient open area that results in decrease in efficacy. Further, there is also an outer cover which further restricts the access of air to the emanating surface.

Accordingly there is need of a volatile liquid dispensing system that overcomes the above mentioned drawbacks of the prior art.

SUMMARY OF THE INVENTION

The present invention provides a volatile liquid dispensing system. The volatile liquid dispensing system includes a dispenser and a refill unit. The dispenser is mounted on a predefined surface. The predefined surface is any one of a mounting surface and a horizontal flat surface. The dispenser includes a front cover and a rear cover. The front cover is adapted to secure on the rear cover. The refill unit is removably secured inside the dispenser using at least one O-ring and/or at least one flat seal such that a predefined gap is maintained therebetween. The predefined gap between the dispenser and the refill unit is minimum of 5 mm.

The refill unit includes a refill cover. The refill cover includes a fragrance reservoir and a collection device (i.e. collector) enclosed therein. The fragrance reservoir is positioned in a predefined orientation with respect, to the predefined surface. The fragrance reservoir delivers the volatile liquid to the collection device through a predefined discharging mode. The preferred discharging mode is gas. Alternatively, the discharging mode may be gravity. The collection device is positioned adjacent to the fragrance reservoir thereby maintaining a predefined gap therebetween. The predefined gap between the collection device and the fragrance reservoir is minimum of 5 mm. The collection device is used for collecting and emanating pumped volatile liquid from the fragrance reservoir into an atmosphere. The collection device is enclosed in the refill cover such that, a predefined gap is maintained therebetween thereby allowing evaporation of the volatile liquid from all sides of the collection device. The predefined gap between the collection device and the refill unit is minimum of 2 mm.

In another aspect, the present invention provides a volatile liquid dispensing system that includes only an independent refill unit. The collection device is arranged in such a way that allows exposure of all sides of the collection device to air thereby allowing increased evaporation of the volatile liquid from inside and outside surfaces of the collection device. The system of the present invention is utilised for dispensing any volatile liquid including insecticide, pheromone, micronutrients and the like. The geometric arrangement of the fragrance reservoir and the collection device in the system advantageously enables air flow to all sides of the collection device to take part in the evaporation of the liquid thus ensuring maximum volatile liquid to be delivered to the surroundings.

DETAILED DESCRIPTION OF THE PREFERRED EMBODIMENT

The invention described herein is explained using specific exemplary details for better understanding. However, the invention disclosed can be worked on by a person skilled in the art without the use of these specific details.

References in the specification to "one embodiment" or "an embodiment" means that a particular feature, structure, characteristic, or function described in connection with the embodiment is included in at least one embodiment of the invention. The appearances of the phrase 'in one embodiment in various places in the specification are not necessarily all referring to the same embodiment.

References in the specification to 'preferred embodiment means that a particular feature, structure, characteristic, or function described in detail thereby omitting known constructions and functions for clear description of the present invention.

In general aspect, the present invention describes a volatile liquid dispensing system. The geometric arrangement of a fragrance reservoir and a collection device in the volatile liquid dispensing system enables air flow to all sides of the collection device to take part in the evaporation of the volatile liquid thus ensuring maximum fragrance to be delivered to surroundings. The geometric arrangement of the system is adapted to deliver 0.1 ml/day to 10 ml/hr of fragrance in a consistent or variable fashion without being leaking from the system with maximum transfer of the volatile liquid to a vapour phase to the room being fragranced.

The present invention is illustrated with reference to the accompanying drawings, throughout which reference numbers indicate corresponding parts in the various figures. These reference numbers are shown in bracket in the following description.

Figure 1:
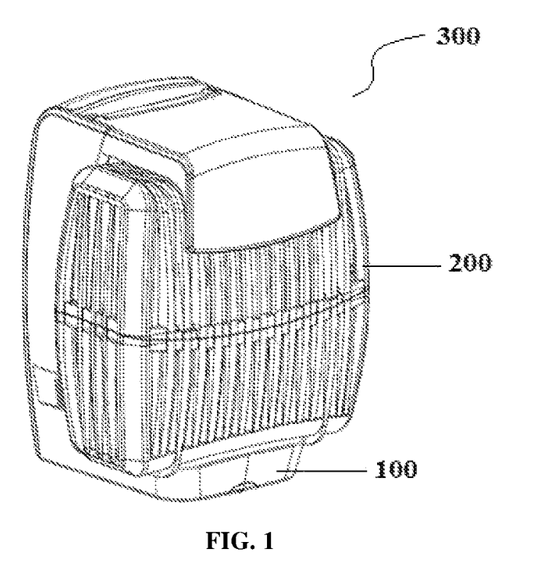
FIG. 1 shows a perspective view of a volatile liquid dispensing system, in accordance with a preferred embodiment of the present invention.
Figure 2:
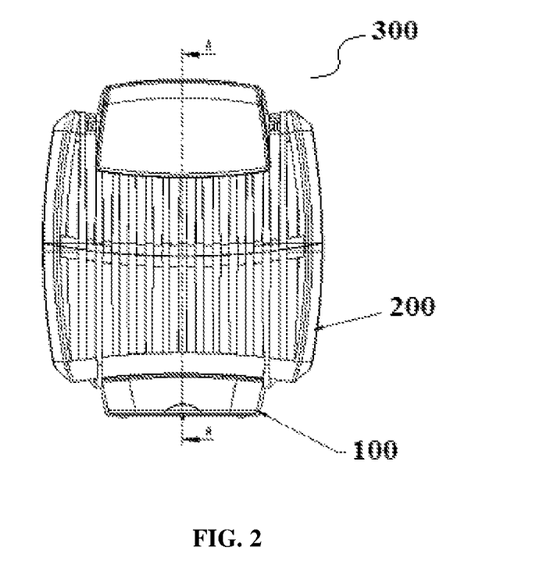
FIG. 2 shows a front view of the volatile liquid dispensing system of FIG. 1.
Figure 3:
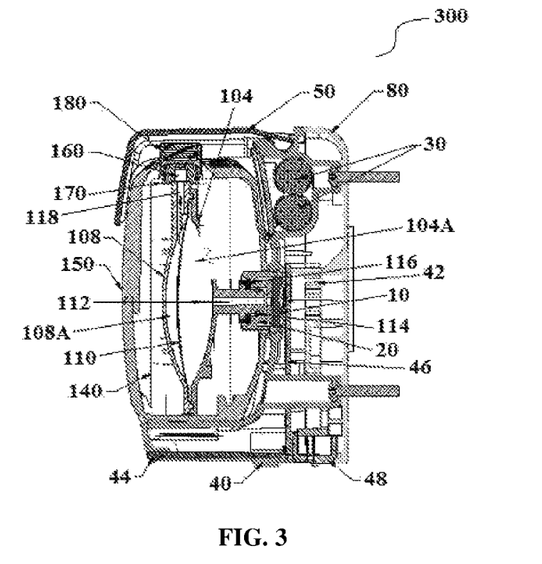
FIG. 3 shows a cross sectional view of the volatile liquid dispensing system of FIG. 2 along a section line A-A.

Referring to FIG. 1-3, a volatile liquid dispensing system (300) (hereinafter 'the system (300)) in accordance with a preferred embodiment of the present invention is shown. In this preferred embodiment, the system (300) includes a dispenser (100) and a refill unit (200). The dispenser (100) is mounted on a predefined surface using screws (85). The predefined surface is any one of a mounting surface and a horizontal flat surface.

Figure 4:
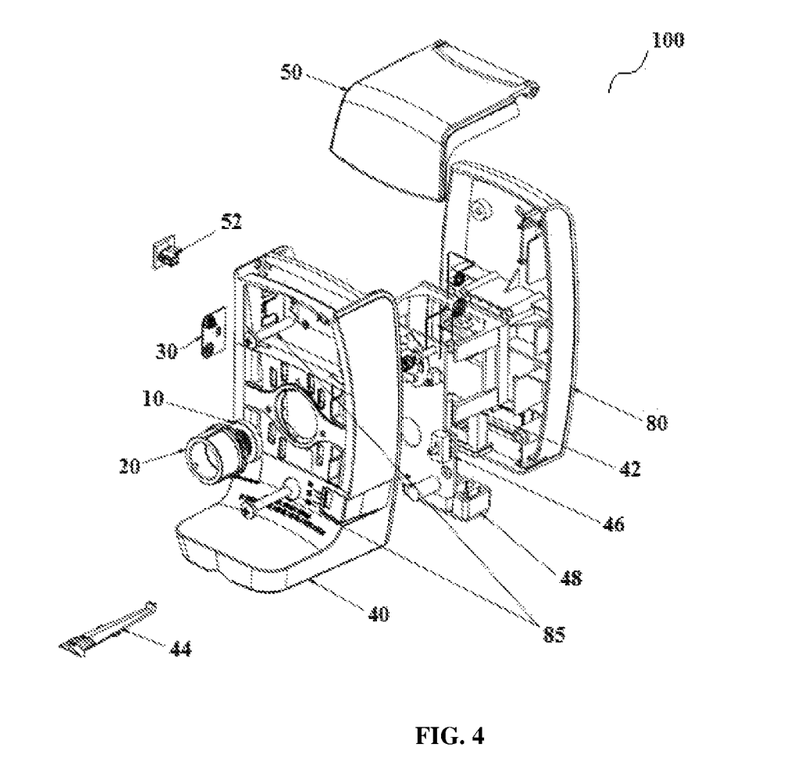
FIG. 4 shows an exploded view of a dispenser of the volatile liquid dispensing system, in accordance with the preferred embodiment of the present invention.

As shown in FIG. 3-4, the dispenser (100) includes a front cover (40) and a rear cover (80). The front cover (40) is adapted to secure on the rear cover (80). The front cover (40) includes a generator subassembly (20) and a pair of batteries (30). The generator subassembly (20) is secured to the front cover (40) using screws. The generator subassembly (20) includes a gas generating device (10) enclosed therein. In this one embodiment, the gas generating device (10) is an oxygen generator. However, it is understood here that the gas generating device may include carbon dioxide generator, hydrogen generator, nitrogen generator and any other suitable gas generating device in other alternative embodiments of the system (300). The pair of batteries (30) is enclosed in the front cover (40). In another embodiment, the dispenser (100) may be fully exposed with minimal front cover and rear cover.

The rear cover (80) includes a snap section (42), a printed circuit board (46) (hereinafter "PCB (46)"), a modular lock (48) and a top flap (50). The snap section (42) includes a plurality grooves and ribs configured on an end thereof. The refill unit (200) is snap fitted into the plurality of grooves of the snap section (42). The PCB (46) is mounted on the snap section (42) using screws. The PCB (46) is powered by the pair of batteries (30). The PCB (46) includes a current controlling circuitry that provides constant/variable pattern current supply to the gas generating device (10). The PCB (46) includes a detector switch and a plurality of light emitting diodes (LED). The detector switch is used to identify the presence of the refill to start the gas generation. The LED is used to provide user with information about status of fluid delivery/battery low and refill change information. The light from the LED on the PCB (46) is extended to a front side of the front cover (40) through a pipe (44). The PCB (46) also includes a buzzer. The buzzer alerts the user for refill change or regarding alarm conditions in the system (300) such as when the battery is empty or in case of fault in the gas generator. A buzzer on/off switch (52) is used to mute the buzzer.

The modular lock (48) is operated by a key and provides access to the snap section (42). When the key is inserted in the modular lock (48), the snap section (42) gets pressed by the key thereby causing movement of the snap section (42) resulting in disengagement of the refill unit (200) from the snap section (42). The top flap (50) closes a piercing area of the dispenser (100) and also serves as a branding space for the system (300). In another embodiment, the system (300) includes a push button instead of the modular lock (48). The push button allows the operator to access the snap section (42) without a key just by pressing the push button.

In another embodiment of the system (300), the dispenser (100) is designed in a modular fashion such that the push button version or the modular lock version can be achieved by exchange of modules at the customer or factory level.

Figure 5:
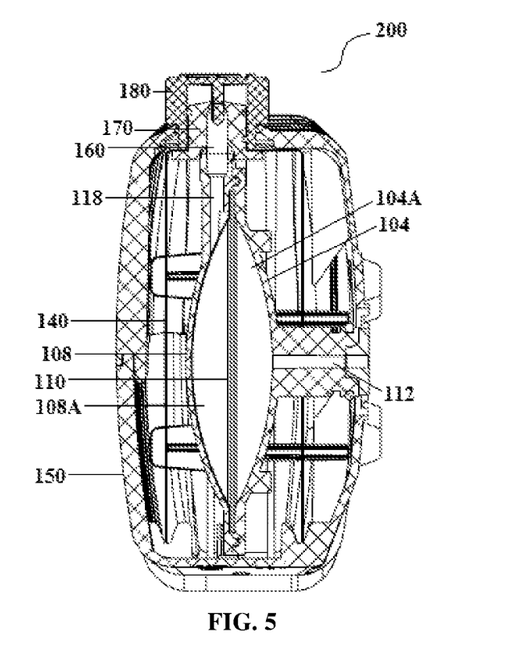
FIG. 5 shows a cross sectional view of a refill unit of the volatile liquid dispensing system, in accordance with the preferred embodiment of the present invention.
Figure 6A:
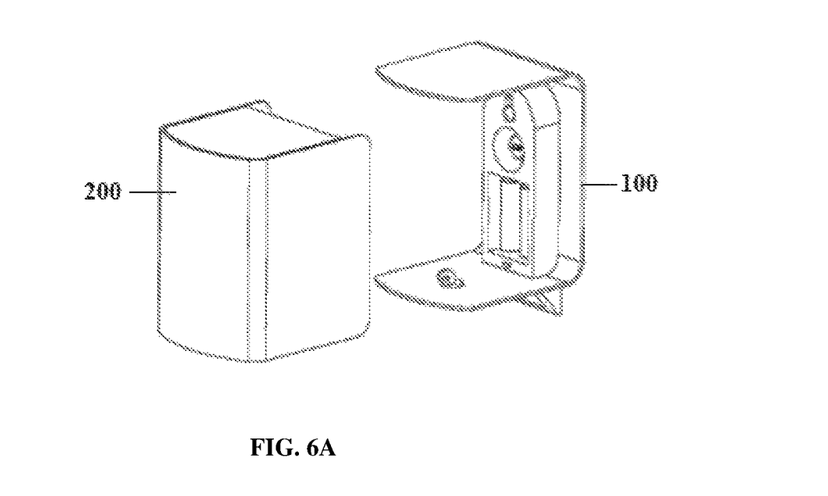
FIG. 6A is an exploded assembly view showing the dispenser and the refill unit of the volatile liquid dispensing system, in accordance with the preferred embodiment of the present invention.
Figure 6B:
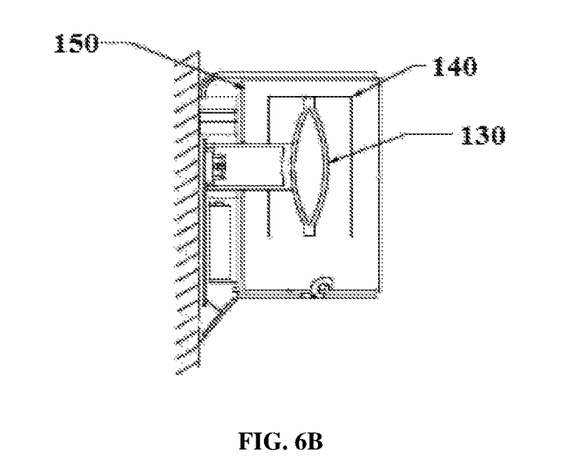
FIG. 6B shows an arrangement of a fragrance reservoir of the volatile liquid dispensing system, in accordance with the preferred embodiment of the present invention.

The refill unit (200) is secured inside the dispenser (100) such that a predefined gap is maintained therebetween. In an embodiment, minimum of 5 mm space is maintained between the refill unit (200) and the front cover (40) of the dispenser (100) with ample openings for air flow. As shown in FIG. 5, the refill unit (200) includes a refill cover (150), a threaded cap (170) and a piercing cap (180). The refill cover (150) includes a fragrance reservoir (130) and a collection device (140) enclosed therein. The fragrance reservoir (130) is positioned in a predefined orientation with respect to the predefined surface. In this one embodiment, the fragrance reservoir (130) is positioned in a parallel orientation with respect to the mounting surface (FIG. 6B). It is, understood here that the orientation is considered by assuming that the refill unit (200) is mounted on a wall so that a floor is perpendicular to the mounting surface (FIG. 6A). The fragrance reservoir (130) delivers the volatile liquid to the collection device (140) through a predefined discharging mode. In this one embodiment, the discharging mode is gas. However, it is understood that the discharging mode may be gravity in other alternative embodiments of the system (300).

The fragrance reservoir (130) is formed by a gas shell (104) and a fragrance shell (108). The gas shell (104) and the fragrance shell (108) include a pliable membrane (110) sandwiched therebetween thereby defining a gas side (104A) and a fragrance side (108A) with respect to the fragrance reservoir (130). The gas side (104A) of the fragrance reservoir (130) includes an inlet (112), an O-ring (114) and a flat seal (116). The inlet (112) allows passage of gas from the gas generating device (10) to the gas shell (104). In the context of the present invention, the refill unit (200) is secured inside the dispenser (100) using at least one O-ring (114) and/or at least one flat seal (116).

The fragrance side (108A) of the fragrance reservoir (130) includes an outlet (118) that extends to a restriction section (160). The restriction section (160) is housed in the threaded cap (170). The threaded cap (170) has a thin film that protects the fragrance from being spilled till the users wants use thereof. The piercing cap (180) includes predefined threads on either side thereof. The predefined threads on one side of the piercing cap (180) engage with the threaded cap (170) and facilitate piercing of the thin film of the threaded cap (170). The predefined threads on other side of the piercing cap (180) close the outlet (118) when flipped by 180 degrees.

The collection device (140) is positioned adjacent to the fragrance reservoir (130) such that a predefined gap is maintained therebetween. In an embodiment, minimum of 5 mm space is left between the collection device (140) and the fragrance reservoir (130) in order to allow unhindered air flow. The collection device (140) includes a cellulose or porous plastic with minimum thickness as possible in order to reduce retention of the volatile liquid fragrance therein. The collection device (140) is used to collect and emanate the pumped fragrance from the fragrance reservoir (130). In this one embodiment, the area required for delivery of 1 ml/day of the volatile liquid is about 160 cm$^2$ of cellulose based collection device (140). The collection device (140) is enclosed in the refill unit (200) such that a predefined gap is maintained therebetween. In an embodiment, minimum of 2 mm space is left between the collection device (140) and refill unit (200) in order to allow unhindered air flow. The collection device (140) is arranged in such a way that allows exposure of all sides of the collection device (140) to air thereby allowing increased evaporation of the volatile liquid from inside and outside surfaces of the collection device (140).

Figure 7A:
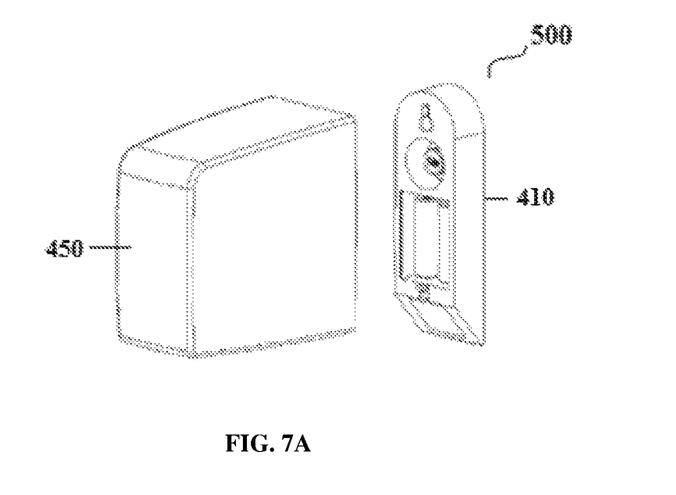
FIG. 7A is an exploded assembly view showing a dispenser and a refill unit of a volatile liquid dispensing system, in accordance with another embodiment of the present invention.
Figure 7B:
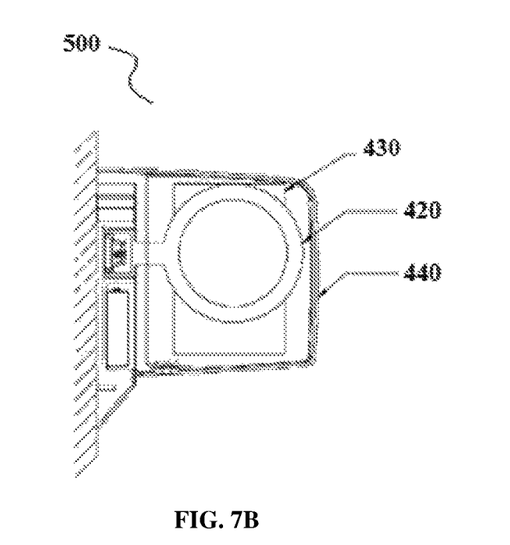
FIG. 7B shows an arrangement of a fragrance reservoir of the volatile liquid dispensing system, in accordance with another embodiment of the present invention.

Referring to FIG. 7A-7B, a volatile liquid dispensing system (500) (hereinafter "the system (500)") in accordance with another embodiment of the present invention is shown. The system (500) comprises a dispenser (410) and a refill unit (450). The refill unit (450) includes a refill cover (440). The refill cover (440) includes a fragrance reservoir (420) and a collection device (430). In this one embodiment, the fragrance reservoir (420) is positioned in a perpendicular orientation with respect to a mounting surface such that the fragrance reservoir (420) is also in a perpendicular orientation with respect to a floor.

Figure 8A:
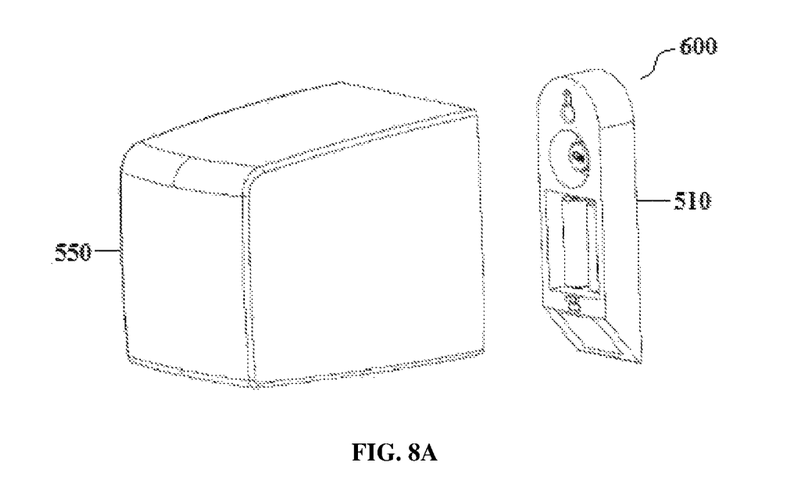
FIG. 8A is an exploded assembly view showing a dispenser and a refill unit of a volatile liquid dispensing system, in accordance with yet another embodiment of the present invention.
Figure 8B:
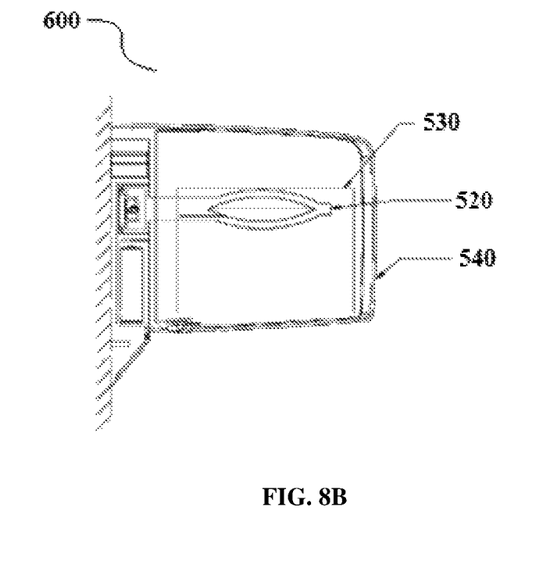
FIG. 8B shows an arrangement of a fragrance reservoir of the volatile liquid dispensing system, in accordance with yet another embodiment of the present invention.

Referring to FIG. 8A-8B, a volatile liquid dispensing system (600) (hereinafter "the system (600)") in accordance with another embodiment of the present invention is shown. The system (600) comprises a dispenser (510) and a refill unit (550). The refill unit (550) includes a refill cover (540). The refill cover (540) includes a fragrance reservoir (520) and a collection device (530). In this one embodiment, the fragrance reservoir (520) is positioned in a parallel orientation with respect to a mounting surface such that the fragrance reservoir (420) is also in a parallel orientation with respect to a floor.

In another embodiment, the system includes only the refill unit and does not include the dispenser. In this one embodiment, the gas generation device is a part of the refill unit and derives power from a power source. The power source is selected from solar power, gravity, batteries such as silver oxide, zinc air, alkaline, lithium and any other suitable power source. After the volatile liquid is spent, the refill unit is removed and replaced with a new refill unit.

In yet another embodiment, the system includes the gas generation device with the refill unit. In this one embodiment, the dispenser includes the pair of batteries enclosed therein for providing power to the gas generation device.

Referring again to FIG. 1-5, in operation, a user takes new refill unit (200) having the piercing cap (180) screwed on in a sealing condition. The user unscrews the piercing cap (180) of the refill unit (200). The user then flips the piercing cap (180) by 180 degrees and screws back the piercing cap (180) on to the threaded cap (170) thereby causing rupture of the thin film of the threaded cap (170). The refill unit (200) is then inserted into the dispenser (100) where the O-ring (114) and the flat seal (116) engage with the generator sub assembly (20) thereby forming a gas tight seal. At the same time, the detector switch on the PCB (46) gets pressed by the refill unit (200) that activates the gas generating device (10) by starting initiating current supply to the generator subassembly (20) and also starting the indication of LED sequence. The generated gas passes through the inlet (112) into to the gas shell (104) of the fragrance reservoir (130).

As the outlet (118) of the fragrance side of the fragrance reservoir (130) is open to the atmosphere due to the piercing action, the gas entering the gas shell (104) puts pressure on the pliable membrane (110) thereby pushing an equivalent volume of the volatile liquid through the outlet (118) in order to maintain pressure equilibrium on either side of the pliable membrane (110). The displaced volume of the volatile liquid passes through the restriction section (160) and drops into channels of the threaded cap (170) that further leads to the collection device (140). The fragrance then evaporates from the collection device (140) into the air.

The system (300) of the present invention allows maximum transfer of the volatile liquid/fragrance into the air thus increasing the efficacy. The system (300) of the present invention is energy efficient and cost effective. The system (300) of the present invention is utilised for dispensing any volatile liquid including insecticide, pheromone, micronutrients and the like. The geometric arrangement of the fragrance reservoir (130) and the collection device (140) in the system (300) advantageously enables air flow to all sides of the collection device (140) to take part in the evaporation of the liquid thus ensuring maximum fragrance to be delivered to the surroundings. The different orientations of the fragrance reservoir (130) with respect to the mounting surface and the floor advantageously enable the collection device (140) to have maximized air flow and thus provide maximum evaporation and increased efficacy of the system (300). Due to geometric arrangement of the fragrance reservoir (130) and the collection device (140), the system (300) prevents leaking as well as pooling of the volatile liquid. The system (300) is made available in smaller package size due to improved evaporation for the same quantity of volatile liquid/fragrance pumped out on to the collection device (140) in comparison to the existing systems. The geometry and design of the collection device (140) with respect to the fragrance reservoir (130) is such that both sides of the collection device are exposed to air flow thereby enabling maximum evaporation.

The foregoing description of specific embodiments of the present invention has been presented for purposes of illustration and description. They are not intended to be exhaustive or to limit the present invention to the precise forms disclosed, and obviously many modifications and variations are possible in light of the above teaching.

The embodiments were chosen and described in order to best explain the principles of the present invention and its practical application, to thereby enable others, skilled in the art to best utilize the present invention and various embodiments with various modifications as are suited to the particular use contemplated.

It is understood that various omission and substitutions of equivalents are contemplated as circumstance may suggest or render expedient, but such are intended to cover the application or implementation without departing from the scope of the present invention.

What is claimed is:

1. A volatile liquid dispensing system comprising:
   a dispenser mounted on a predefined surface, the dispenser having a front cover and a rear cover, the front cover secured on the rear cover; and
   a refill unit removably secured inside the dispenser thereby maintaining a first predefined gap therebetween, the refill unit comprising a refill cover, and a fragrance reservoir and a collector enclosed therein,
   wherein the fragrance reservoir contains fragrance as a volatile liquid and is positioned in a predefined orientation with respect to the predefined surface, said fragrance reservoir being configured to deliver the volatile liquid to the collector through a predefined discharge mode,
   wherein the collector is a sheet of cellulose/porous plastic/other absorbent porous materials bent or molded to form flat or/and curved portions positioned around the fragrance reservoir with a second predefined gap of at least 5 mm maintained between the collector and the fragrance reservoir and a third predefined gap of at least 2 mm maintained between the collector and the refill cover, said collector comprises an opening between the refill cover and the fragrance reservoir, and the second predefined gap is open to the third predefined gap through the opening, said collector comprising a top portion, a first side portion and a second side portion, wherein the first side portion and second side portion are opposite each other, said collector being open at a bottom and at least one side perpendicular to the first and second sides, such that all sides of the collector are exposed to air, which flows unhindered on all sides of the collector, thereby allowing increased evaporation of the volatile liquid from inside and outside surfaces of the collector, wherein the top portion of the collector is positioned farther than the bottom of the collector from a floor or a ground,
   the collector being configured for collecting the volatile liquid delivered from the fragrance reservoir and emanating the volatile liquid into an atmosphere, wherein the fragrance reservoir comprises an outlet on a top portion thereof, and the volatile liquid passes through the outlet on the top portion of the fragrance reservoir from inside of the fragrance reservoir to the top portion of the collector.

2. The volatile liquid dispensing system as claimed in claim 1, wherein the discharging mode is gas released from a gas generator in the dispenser.

3. The volatile liquid dispensing system as claimed in claim 1, wherein the discharging mode is gravity.

4. The volatile liquid dispensing system as claimed in claim 1, wherein the predefined surface is any one of a mounting surface and a horizontal flat surface.

5. The volatile liquid dispensing system as claimed in claim 1, wherein the fragrance reservoir is positioned in a parallel orientation with respect to the predefined surface.

6. The volatile liquid dispensing system as claimed in claim 1, wherein the fragrance reservoir is positioned in a perpendicular orientation with respect to the predefined surface.

7. The volatile liquid dispensing system as claimed in claim 1, wherein the refill unit is secured inside the dispenser using at least one O-ring and/or at least one flat seal.

8. A volatile liquid dispensing system comprising a refill unit, the refill unit comprising a refill cover, and a fragrance reservoir and a collector enclosed therein,
   wherein the fragrance reservoir contains fragrance as a volatile liquid and is positioned in a predefined orientation with respect to the predefined surface, said fragrance reservoir being configured to deliver the volatile liquid to the collector through a predefined discharge mode,
   wherein the collector is a sheet of cellulose/porous plastic/other absorbent porous materials bent or molded to form flat or/and curved portions positioned around the fragrance reservoir with a second predefined gap of at least 5 mm maintained between the collector and the fragrance reservoir and a third predefined gap of at least 2 mm maintained between the collector and the refill cover, said collector comprises an opening between the refill cover and the fragrance reservoir, and the second predefined gap is connected to the third predefined gap by the opening, said collector comprising a top portion, a first side portion and a second side portion, wherein the first side portion and second side portion are opposite each other, said collector being open at a bottom and at least one side perpendicular to the first and second sides, such that all sides of the collector are exposed to air, which flows unhindered on all sides of the collector, thereby allowing increased evaporation of the volatile liquid from inside and outside surfaces of the collector, wherein the top portion of the collector is positioned farther than the bottom from a floor or a ground, the collector being configured for collecting the volatile liquid delivered from the fragrance reservoir and emanating the volatile liquid into an atmosphere, wherein the fragrance reservoir comprises an outlet on a top portion thereof, and the volatile liquid passes through the outlet on the top portion of the fragrance reservoir from inside the fragrance reservoir to the top portion of the collector.

9. The volatile liquid dispensing system as claimed in claim 8, wherein the discharging mode is gas released from a gas generator in the refill unit.

10. The volatile liquid dispensing system as claimed in claim 8, wherein the discharging mode is gravity.

\* \* \* \* \*